United States Patent [19]

Quinn et al.

[11] Patent Number: 4,529,102

[45] Date of Patent: Jul. 16, 1985

[54] ENTERIC FEEDING BAG

[75] Inventors: David G. Quinn, Grayslake; Robert B. Edwards, II, Libertyville; Erik Andersen, Vernon Hills, all of Ill.

[73] Assignee: Viridian, Inc., Wheeling, Ill.

[21] Appl. No.: 460,073

[22] Filed: Jan. 21, 1983

Related U.S. Application Data

[63] Continuation-in-part of Ser. No. 381,353, May 24, 1982, abandoned.

[51] Int. Cl.[3] .............................................. A61M 5/14

[52] U.S. Cl. ..................................... 222/94; 222/456; 222/481; 604/262; 604/410

[58] Field of Search .................. 222/92, 94, 107, 481, 222/478, 454–456, 527–528, 420, 422; 604/246, 122, 124, 262, 408–410, 77, 325; 383/9, 35, 25, 66; 206/829

[56] References Cited

U.S. PATENT DOCUMENTS 2,969,063 1/1961 Broman .............................. 604/246
2,999,387 9/1961 Andelin ........................... 383/66 X
3,090,532 5/1963 Robson ............................. 222/456
3,239,096 3/1966 Buono et al. .................. 604/262 X
3,985,135 10/1976 Carpenter .......................... 604/410
4,432,763 2/1984 Manshot et al. .................... 604/262

*Primary Examiner*—Charles A. Marmor
*Attorney, Agent, or Firm*—Robert E. Wagner; Alan L. Barry

[57] ABSTRACT

An enteric feeding bag having unique fluid dispensation features comprising a supplying chamber within the bag being coupled to an inlet, a feeding chamber of smaller volume than the supplying chamber being coupled to an inlet, a feeding chamber of smaller volume than the supplying chamber being coupled to an outlet, a channel placing the chambers in selective fluid communication upon tilting of the bag, a partition between the chambers having at least one aperture to receive a clamp in which the aperture coincides with volumetric graduations on the feeding chamber, an elongated flap appended to the exterior peripheral edge of the feeding chamber also having at least one aperture horizontally coinciding with the aperture on the partition and, a clamp inserted through the apertures for transversely sealing together the side walls of the feeding chamber at one aperture.

16 Claims, 16 Drawing Figures

FIG. 5
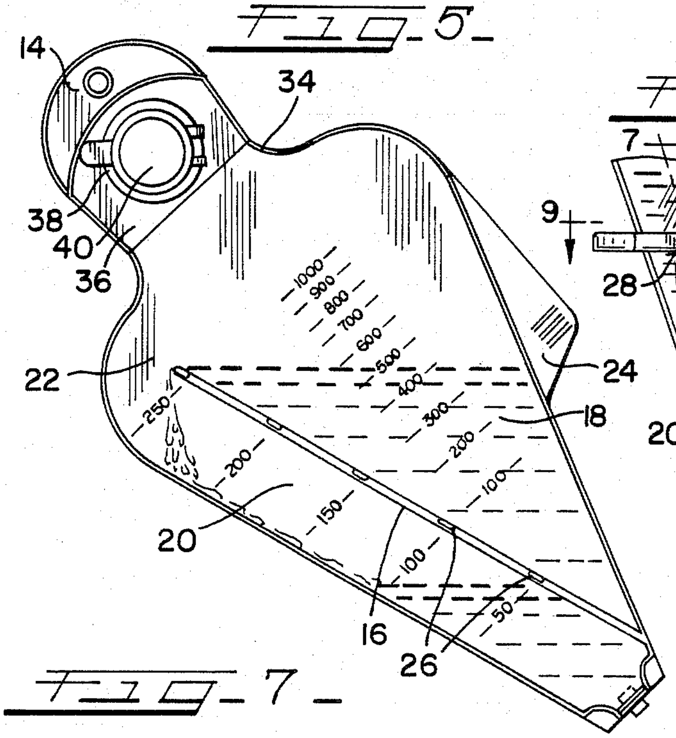
FIG. 6
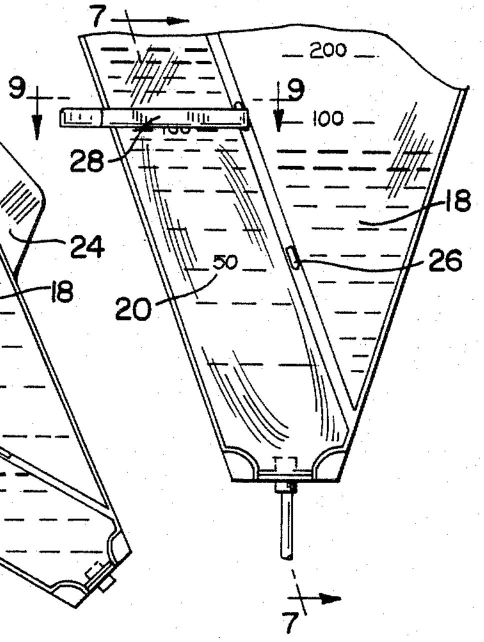
FIG. 7
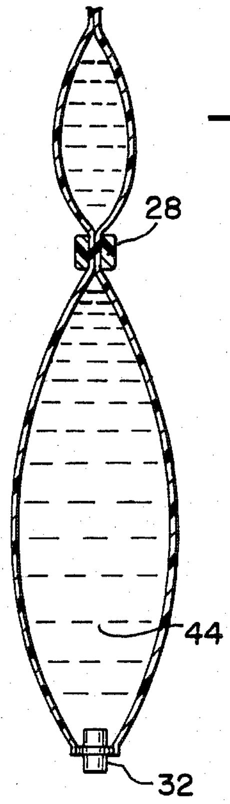
FIG. 8
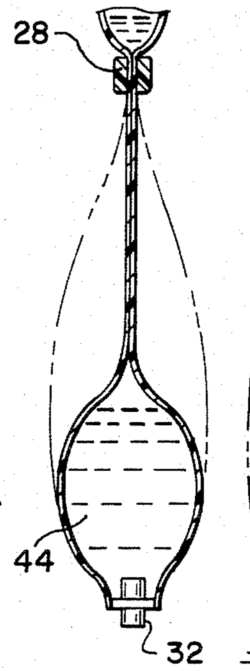
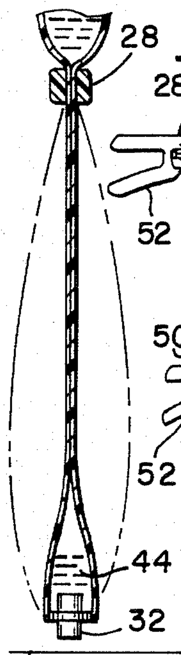
FIG. 8A
FIG. 10
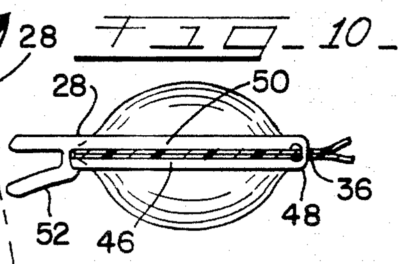
FIG. 9
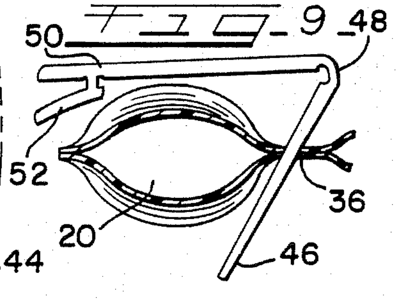

ENTERIC FEEDING BAG

REFERENCE TO RELATED APPLICATION

This application is a continuation-in-part of application Ser. No. 381,353, filed May 24, 1982 now abandoned.

TECHNICAL FIELD

The present invention generally relates to enteric feeding of fluid to a patient, and in particular to an improved enteric feeding bag for use with a drip chamber, administration tubing and enteric feeding tubing.

BACKGROUND OF THE INVENTION

During the medical treatment of some patients, it becomes necessary for a patient to undergo enteric therapy by receiving fluid nutrient or medical preparations through a flexible feeding tube having a very small cross-sectional diameter. Feeding tubes are inserted either orally or nasally, the tube passing through the esophagus and resting within the patient's stomach or duodenum. Typically, feeding tubes are necessary for patients who are unable to swallow or have difficulty masticating, but nevertheless have functional gastrointestinal tracts. An essential component in enteric therapy for use in combination with a feeding tube is a distensible feeding bag to contain a selected quantity of fluid. Generally, a feeding bag is suspended from an upright frame or hanger to permit gravity feeding of the fluid contained within the bag.

Prior art feeding bags generally have an outlet positioned along the bottom edge of the bag into which the proximal end of a feeding tube administration apparatus is inserted. Such apparatuses generally include a segment of administration tubing having a cross-sectional diameter greater than the feeding tube, a drip chamber interposed along the length of the administration tube and a connector to join the administration tube to the feeding tube.

The rate of flow of fluid from the feeding bag into the feeding tube is usually controlled and limited by securing a tube set clamp, of either a roller or screw type, onto the administration tube. Such clamping permits adjustment of the rate of fluid flow according to the physician's specification. A problem with prior art enteric feeding bags occurs if the set clamp is improperly adjusted or if the clamp becomes disengaged entirely resulting in an uncontrolled rate of fluid input to the patient. High rates of flow cause inundation or "bolus" feeding with the obvious adverse effect of the patient receiving an entire supply of fluid contained within the bag over a short period of time. The amount of fluid received by a patient in bolus feeding may be significant since many standard enteric feeding bags may be 1,000 milliliters in volume or more. Hence, a need existed for an enteric feeding bag which by design can limit the amount of fluid dispensed.

Moreover, if a health care attendant is not present to disengage a prior art feeding bag at the conclusion of a feeding period, the bag will become totally void of fluid and the patient will begin to ingest air or vapor remaining within the bag. Hence, a need also existed for an enteric feeding bag which will automatically cease feeding fluid to a patient thereby preventing ingestion of air upon total fluid evacuation of the bag.

Finally, prior art distensible feeding bags often incur problems with constant flow rates from the bags resulting from configurational distortion of the peripheral edges of the bags from both the weight and volume of fluid contained within the bag. A need therefore existed for an enteric feeding bag which continues to maintain its peripheral configuration irrespective of the amount of fluid contained therein.

SUMMARY OF THE INVENTION

According to the present invention, a distensible enteric feeding bag for fluid feeding of a patient has been developed which limits and controls dispensation of the fluid contents of the bag. Further, the present invention passively retains a small residue of fluid at the bottom of the bag to prevent the bag from becoming totally void of fluid and ceasing fluid dispensation so that a patient will not ingest air.

Generally, the present invention embodies an enteric feeding bag comprised of two chambers, a feeding chamber and a supplying chamber. The chambers may be in fluid communication with each other depending on the orientation of the bag as the chambers are separated by an upwardly extending, impermeable partition. The feeding chamber is of lesser volume than the supplying chamber and is coupled with the outlet of the bag so that the amount of fluid ingested by a patient is limited to the quantity of fluid within the feeding chamber. The partition between the chambers is provided with several discrete openings spaced along the length of the partition, each opening coinciding with a specific volume of the feeding chamber. Any of such openings may receive an elongated, closable clamp to seal transversely and apportion a selected volume of the feeding chamber. In the preferred embodiment of the present invention, several discrete openings are also placed on an elongated flap attached to the peripheral edge of the feeding chamber opposite the partition so that the flap is parallel to the partition. The openings on the peripheral edge flap are in horizontal alignment with the openings in the partition so that each opening may receive a portion of the closable clamp. The elongated flap provides reinforcement to the peripheral configuration of the feeding chamber to insure constant fluid dispensation from the chamber despite the volume of fluid contained therein. In an alternate embodiment, semi-rigid rods are vertically inserted into both the partition and the peripheral edge flap to additionally assure retention of feeding chamber configuration.

The air-tight sealing-off of a selected volume of the feeding chamber isolates such volume from the rest of the bag and results in air pressure within the apportioned volume which is lower than the ambient air pressure. Hence, as fluid drains out of the apportioned volume, the side walls of the feeding chamber surrounding the apportioned volume progressively collapse inward in response to the greater ambient air pressure to trap and retain a small residue of fluid at the bottom of the feeding chamber. Through this arrangement, the feeding chamber will not become completely void of fluid preventing a patient from ingesting air at the conclusion of a given fluid feeding period.

The present feeding bag further includes a tapered neck of lesser cross-sectional dimensions than the main body of the bag. At the neck, the front wall of the body is collapsibly enfolded with preferred inlet valve being centrally mounted on the outward fold surface. The fold may be used to develop a throat in the supplying chamber permitting a health care attendant to more easily pour fluid into the supplying chamber. In a non-operative position, the throat-forming fold and consequently the inlet valve lie substantially flat enhancing storage of unused feeding bags. To use the throat-forming fold a user grips the neck of the bag under the inlet valve, sliding his thumb under the fold to pivot the fold 90° so that the inlet valve is perpendicularly disposed to the main body of the bag.

With the other hand, the user pulls downward on the bottom of the bag while maintaining the positioning of the throat-forming fold thereby causing each side wall of the supplying chamber to flex outward forming a throat in the supplying chamber. Because of the shape-retaining properties of the preferred plastic from which the present invention is manufactured, the throat remains in the supplying chamber even after the user ceases pulling downward on the bottom of the bag. This permits the user to free one hand in order to pour fluid into the supplying chamber.

The present invention is further described and disclosed through a preferred embodiment presented in the drawings and set forth below in the written description.

BRIEF DESCRIPTION OF THE DRAWINGS

FIG. 5 is a front view illustrating the manner in which the present feeding bag is oriented to pour fluid from the supplying chamber into the feeding chamber;

FIG. 6 is a detailed fragmentary front view of the lower portion of the present feeding bag illustrating the arrangement by which an elongated clamp sealably apportions-off a selected volume of the feeding chamber;

FIG. 7 illustrates a fragmentary side view taken along line 7—7 of FIG. 6;

FIG. 8 is a vertical section taken along line 8—8 of FIG. 6;

FIG. 8*a* is the same view as FIG. 8 illustrating the inward collapsing of side walls of the apportioned volume of the chamber;

FIG. 9 is a horizontal section taken along line 9—9 of FIG. 6 illustrating the method in which the clamp is inserted through a feeding chamber apperture;

FIG. 10 is the same view as FIG. 9 illustrating the arrangement by which the preferred clamp of the present invention transversely seals off a selected volume of feeding chamber;

DETAILED DESCRIPTION

Figure 1:
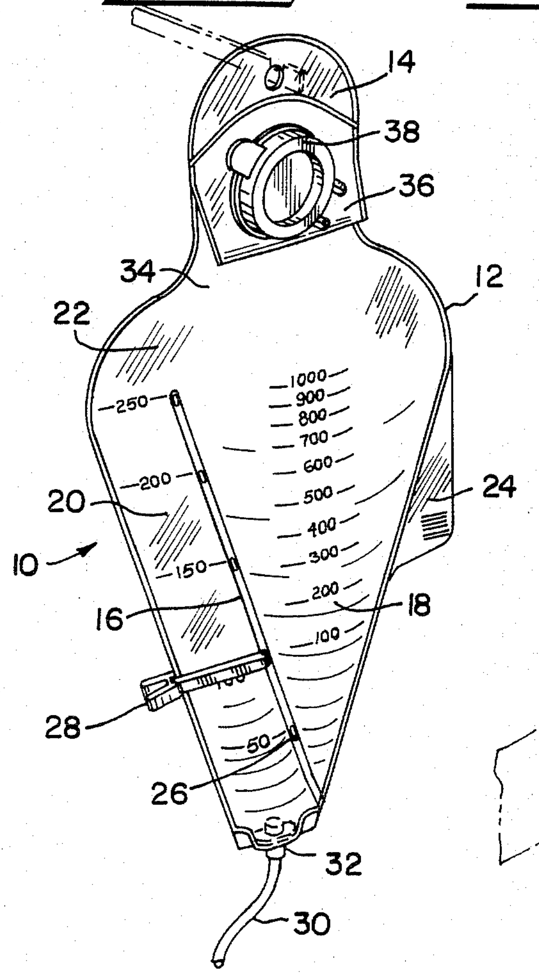
FIG. 1 is a perspective view of one embodiment of the enteric feeding bag of the present invention.

Referring to the drawings, FIG. 1 illustrates one embodiment of the improved enteric feeding bag of the present invention generally referenced by 10. Enteric feeding bag 10 has an overall peripheral configuration similar to a funnel and preferably is manufactured from elastomeric plastics such as polypropylene, polyethylene and polyvinylchloride. The plastic sheets comprising opposing side walls of feeding bag 10 are heat-sealed along side peripheral edges 12. Since feeding bag 10 is suspended from an upright suspension frame (shown in phantom in FIG. 1) to effect the gravity feeding of fluid contents, bag 10 is further provided with a hanger piece 14 through which a portion of a suspension frame may be inserted.

FIG. 1 discloses feeding bag 10 as having a partition 16 which angularly extends upward from the bottom of bag 10 to divide bag 10 into a supplying chamber 18 and a feeding chamber 20. Partition 16 is non-coinciding with the top of feeding bag 10 to define a channel 22 that places supplying chamber 18 and feeding chamber 20 in fluid communication upon selective orientation and tilting of bag 10. By tilting feeding bag 10 to a selected determinate position, such as that shown in FIG. 5 (such determinate position being other than a normal upright operative position of bag 10) fluid contained within supplying chamber 18 pours through channel 22 and into feeding chamber 20. To assist in tilting bag 10 to a selected determinate position, bag 10 is provided with a semi-rigid gripping fin 24 intermediately positioned and attached to the peripherial side edge of bag 10 adjacent to supplying chamber 18.

Partition 16 has several discrete appertures 26 spaced along the length of partition 16. Each aperture 26 coincides with a specific volume of feeding chamber 20. Such apertures 26 are of sufficient dimension to receive a closable clamp 28 which may be inserted through one of apertures 26 to apportion and impermeably seal-off a selected volume of feeding chamber 20. Through this arrangement, bag 10 will dispense only that fluid contained within the apportioned volume of feeding chamber 20 avoiding any problems incurred through improper engagement or disengagement of a set-clamp secured to administration tube 30 inserted into outlet 32. FIG. 1 illustrates that a volume of 100 milliliters of feeding chamber 20 has been sealably apportioned. Because clamp 28 creates an air-tight and impermeable seal, a negative air pressure differential is created between the ambient air pressure and the pressure within the apportioned volume of feeding chamber 20. Such pressure differential causes the opposing side walls surrounding the apportioned volume to collapse inwardly as fluid gradually evacuates feeding chamber 20. Hence, at the conclusion of a feeding period a small volume of fluid is retained at the bottom of feeding chamber 20. Such retention of residual fluid prevents chamber 20 from becoming void of fluid thereby preventing a patient from ingesting air at the conclusion of a feeding period. This passive "valving-off" of feeding chamber 20 will be explained later in greater detail.

Figure 2:
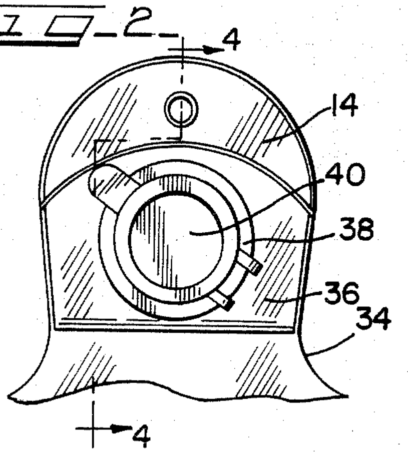
FIG. 2 is a detailed front view of the preferred valved and preferred throat-forming neck fold of the present invention.
Figure 4:
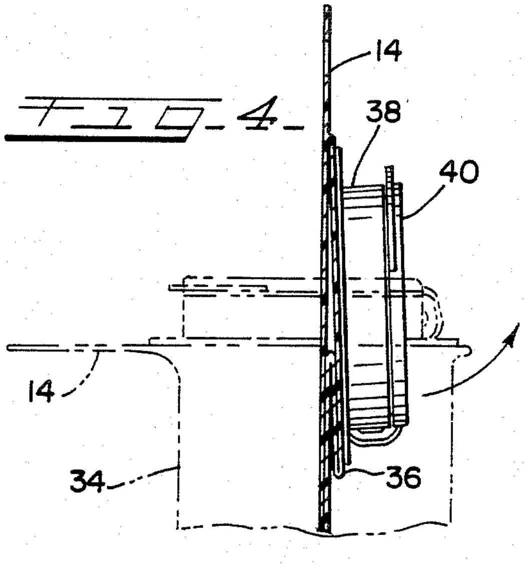
FIG. 4 is a horizontal sectional view taken along line 4—4 of FIG. 2.

FIGS. 1, 2 and 4 disclose that the upper peripheral edges of feeding bag 10 taper inward to provide bag 10 with a neck 34. Incorporated into neck 34 is a collapsable, throat-forming fold 36. Mounted onto fold 36 is a valve 38 having a hingeably attached valve cap 40. Preferably valve 38 is of the type shown in U.S. Pat. No. 2,777,490. As shown in FIG. 4, fold 36 is created by folding under, in pleat-like fashion, an excess portion of an upper part of the front wall of feeding bag 10. Throat-forming fold 36 and valve 38, when in a non-operable position, lie substantially flat and coplanar with the main body of bag 10. Such coplanar positioning of fold 36 and valve 38 permits the present feeding bag to be more easily stored than prior art feeding bags having an inlet valve perpendicularly disposed to the longintudinal axis of the bag.

Figure 3:
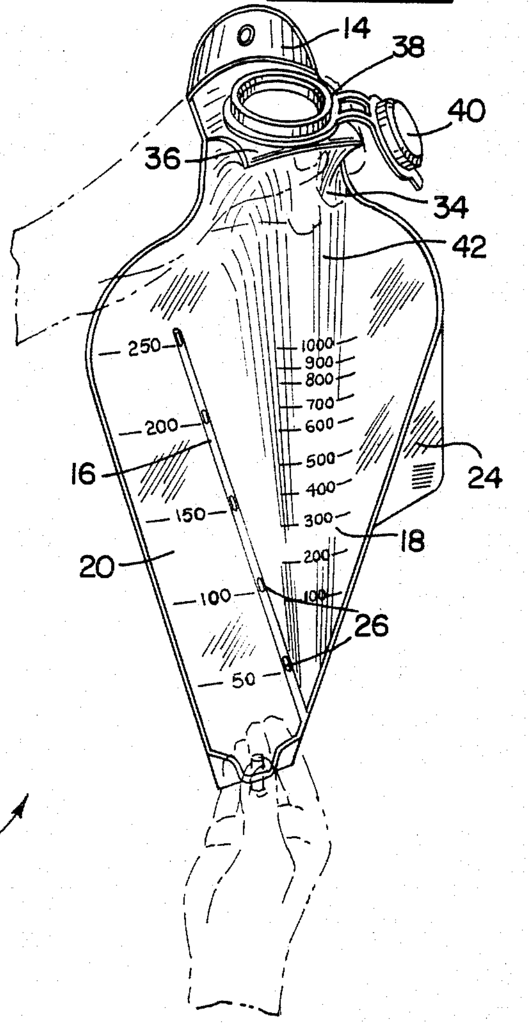
FIG. 3 illustrates the method in which a person may use the throat-forming neck fold of the present invention.

FIGS. 3 and 4 disclose the operational mode of throat-forming fold 36. A health care attendant grips bag 10 around neck 34 and places his thumb under fold 36 to pivot fold 36 approximately 90° so that valve 38 becomes perpendicularly disposed to the longintudinal axis of bag 10. With the other hand, the health care attendant pulls down on the bottom of bag 10 while maintaining the perpendicular positioning of fold 36. Such action downwardly draws bag 10 against fold 36 to cause the side walls of supplying chamber 18 to flex and distend symmetrically outward to develop an elongated throat 42 within supplying chamber 18. Although such downward pulling action causes the side walls of supplying chamber 20 to outwardly distend, such side wall flexing is limited only to the supplying chamber due to partition 16. Further, because of the shape-retaining properties of the elastomeric plastic from which bag 10 is manufactured, the shape of throat 42 is maintained even after a health care attendant ceases pulling down on bag 10. This permits the health care attendant to free one hand in order to pour fluid through valve 38 and into supplying chamber 18. The inclusion of throat-forming fold 36 within bag 10 represents an improvement over prior art feeding bags.

Specifically, since many enteric feeding bags are manufactured from resilient plastics such as polyvinylchloride, newly manufactured bags often carry slight electrostatic charges so that the opposing side walls comprising the bag adhere together making difficult the separation of side walls required to pour fluid into the bag. The throat forming fold 36 in the present invention provides a technique in which the opposing side walls of a newly manufactured enteric feeding may be separated without contamination of the interior of the bag.

FIG. 5 illustrates the method in which fluid is transferred from supplying chamber 18 through channel 22 and into feeding chamber 20. To initiate use of bag 10, a health care attendant pours approximately 1,000 milliliters of fluid nutrient or medicinal preparation into throat 42 of supplying chamber 18; throat 42 being formed by use of fold 36 as previously discussed. Before the first feeding period can commence, it is necessary to charge feeding chamber 20 with a perdetermined quantity of fluid. As previously discussed, in order to fill feeding chamber 20 with a selected quantity of fluid, bag 10 must be tilted to a determinate position so that fluid will flow from supplying chamber 18 through channel 22 into feeding chamber 20. After charging chamber 20 with a selected quantity of fluid, bag 10 is returned to its normal upright operative position.

FIGS. 6 through 8*a* disclose in detail the method in which an elongated closable clamp 28 sealably apportions-off a selected volume of feeding chamber 20 by insertion of clamp 28 through one of apertures 26. Although bag 10 includes several discrete apertures which coincide with selected volumes of feeding chambers 20, it is contemplated that one or, perhaps two elongated apertures extending substantially the length of partition 16 could be employed to receive closable clamp 18 to slideably select a volume of feeding chamber 20 to be apportioned. By using one or two elongated apertures to receive clamp 28, an apportioned volume of feeding chamber 20 may be selected from a greater range of volume rather than the 50, 100, 150, 200 and 250 milliliters volumes shown in FIG. 1.

In the preferred mode of sealably apportioning a selected volume of feeding chamber 20, a health care attendant completely fills feeding chamber 20 with fluid by tilting bag 10 to a determinate position in the manner previously described and disclosed in FIG. 5. Next, the health care attendant selects a volume of feeding chamber 20 to be sealably apportioned with clamp 28. As shown in FIG. 7, this necessarily results in fluid being stored in that portion of feeding chamber 20 above clamp 28 as well as an apportioned volume, referenced by 44, lying between clamp 28 and outlet 32. Although feeding chamber 20 is completely filled with fluid, a patient will only receive that quantity of fluid contained between clamp 28 and the outlet 32 of bag 10. Upon selecting a volume of chamber 20 to be sealed, the health care attendant inserts a portion of clamp 28 into the corresponding aperture 26 in the manner shown in FIG. 9. Clamp 28 is engaged to transversely seal-off the selected volume of feeding chamber 20 in the manner shown in FIG. 10.

By completely filling feeding chamber 20 with fluid before clamping-off a selected volume of chamber 20, a health care attendant virtually eliminates the presence of air within apportioned volume 44. By eliminating the presence of air within apportioned volume 44, a negative air pressure differential is created between the greater ambient air pressure and the lesser air pressure within apportioned volume 44. FIG. 8 illustrates that as fluid gradually evacuates apportioned volume 44, the opposing side walls of feeding chamber 20 gradually collapse inward in response to the greater ambient air pressure. The original positioning of the side walls of feeding chamber 20 are shown in phantom in FIG. 8. Because of the inward collapsing of the side walls a small amount of residual fluid is retained at the bottom of feeding chamber 20. The absence of air within apportioned volume 44 insures that the side walls will collapse sufficiently inward to trap such residual fluid. Since the fluid contents of bag 10 is ingested passively by a patient through gravity feeding the residual of fluid at the bottom of feeding chamber 20, the patient will not ingest air which otherwise would result if feeding chamber 20 became totally void of fluid. Hence, a health care attendant need not be present at the conclusion of a given feeding period since bag 10 passively "valves-off" to cease dispensing fluid to a patient.

A new feeding period is initiated by releasing clamp 38 thereby permitting the fluid retained in the upper portion of feeding chamber 20 above clamp 28 to drop to the bottom of feeding chamber 20. A nurse or other health care attendant tilts bag 10 to charge feeding chamber 20 with additional fluid to permit the sealable apportioning of a selected volume of feeding chamber 20.

FIG. 9 illustrates both the structure of one closable clamp 28 and the method of inserting clamp 28 through one of apertures 36. Clamp 28 is comprised of a first leg 46 joined by a resilient hinge 48 to a second leg 50 having at an opposing end an engaging clasp 52 to latch together first leg 46 with second leg 50. Legs 46 and 50 are preferably designed as elongated flat blades to effectively seal-off a selected volume of feeding chamber 20.

Clamp 28 is preferably molded from a semi-rigid plastic and having sufficient memory so that when legs 46 and 50 are unlatched, clamp 28 remains in the open position shown in FIG. 9.

In using clamp 28 to form a transverse, air-tight seal across chamber 20 at a selected volume, a health care attendant inserts leg 46 through one of apertures 36 and draws leg 46 through until hinge 48 rests within aperture 36. Next, the attendant latches together legs 46 and 50 through use of clasp 52. While it is believed that clamp 28 provides an effective transverse seal across chamber 20, it is of course appreciated that other elongated clamps or fasteners known in the art such as a hemostat could achieve the desired apportionate sealing of chamber 20.

Figure 11:
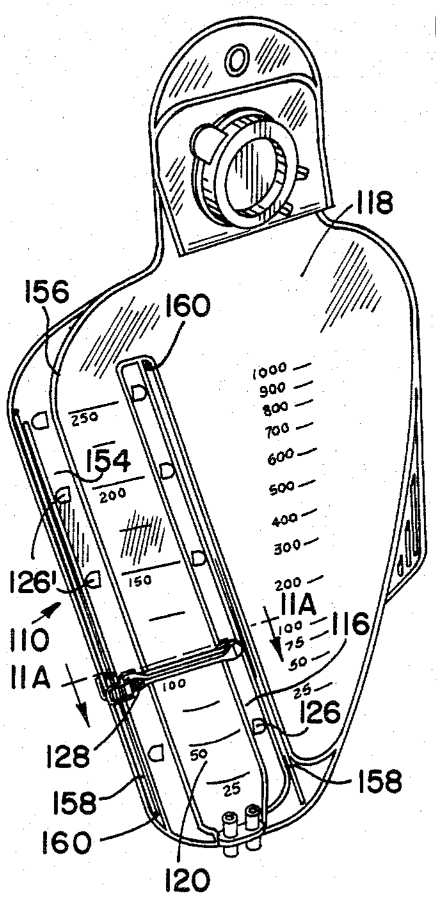
FIG. 11 is a perspective view of another embodiment of the present invention.

FIG. 11 discloses another embodiment of the enteric feeding bag of the present invention, generally referenced by 110. Bag 110 further includes an elongated flap 154 vertically appended to exterior peripheral edge 156 of feeding chamber 120. The inclusion of flap 154 on bag 110 in conbination with partition 116 maintains the peripheral configuration of feeding chamber 120 insuring constant fluid dispensation from feeding chamber 120 irrespective of the volume of fluid therein contained. The peripheral edge distortion of feeding chamber 20 caused by greater volume of fluid in chamber 120, makes difficult the impermeable apportioning-off of feeding chamber 20 by clamp 128 thereby jeopardizing the passive "valving-off" properties of feeding chamber 120. Flap 154 solves this problem by increasing the rigidity of external peripheral edge 156.

Flap 154 further provides an additional set of discrete apertures 126' along the length flap 154 complementing apertures 126 on partition 116. Apertures 126 and 126' are horizontally aligned and positioned at various selected volumetric graduations to permit the sealable apportioning-off of feeding chamber 120 by use of preferred clamp 128.

To further reinforce the peripheral configuration of feeding chamber 120 and to dampen the effects of distortion obtained by the outward distension of the side walls of supplying chamber 118 when a large volume of fluid is contained therein, elongated tubular reinforcement rods 158 are inserted into both flap 154 and partition 116. The incorporation of rods 158 into both flap 154 and partition 116 is acheived through insertion of rods 158 into elongated pockets 160 included within partition 116 and flap 154.

Figure 11A:
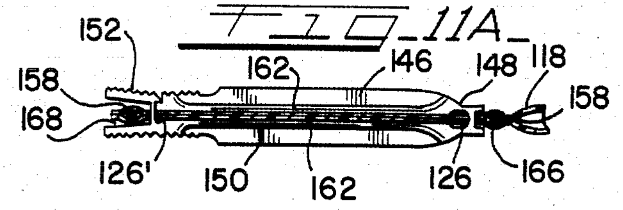
FIG. 11*a* is a horizontal section taken through line 11*a*—11*a* of FIG. 11 showing the preferred elongated clamp in closed position.
Figure 11B:
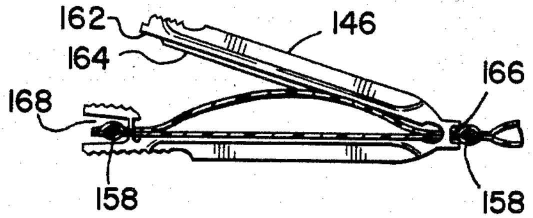
FIG. 11*b* is the same view as FIG. 11*a;*

FIG. 11*a* illustrates the manner in which preferred elongated clamp 128 transversely seals together side walls of feeding chamber 120 to impermeably apportion-off a selected volume of feeding chamber 120. Preferred clamp 128 includes a shorter first leg 146 joined by a resilient hinge 148 to a longer second leg 150 and having an engaging clasp 152 which latches together first leg 146 with second leg 150. Legs 146 and 150 are preferably designed to include flat clamping surfaces 162 to compress together the side walls of feeding chamber 120. FIG. 11*b* further discloses first leg 146 as having a longitudinal ridge 164 substantially extending the length of 146 and across clamping surface 162. Ridge 164 tightly impresses upon the side walls of feeding chamber 120 to ensure that an impermeable transverse seal of feeding chamber 120. Either first leg 146 or second leg 150 should, to a slight degree, be outwardly arcuate to add to the further resilience and clamping properties of preferred clamp 152.

FIGS. 11*a* and 11*b* disclose hinge 148 as having an outwardly directed groove 166 and clasp 152 also having an outwardly directed groove 168. Groove 166 fits within one of apertures 126 of partition of 116 and groove 168 fits within one of apertures 126' of flap 154. Preferrably clamp 128 is slightly longer than the horizontal distance between apertures 126 and 126' so that when clamp 128 is inserted through apertures 126 and 126', grooves 166 and 168 act against the outer edges of apertures 126 and 126' and further abut against reinforement rods 158 to stretch the apertures 126 and 126' further apart. Such stretching tautly draws together the side walls of feeding chamber 120 to form a secure and impermeable transverse seal across a selected portion of feeding chamber 120.

Figure 12:
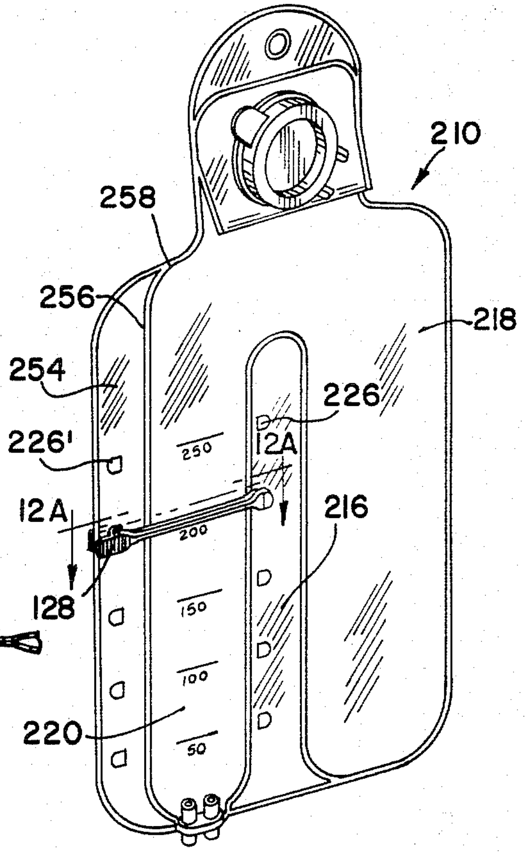
FIG. 12 is a perspective view of the preferred embodiment of the present invention.

Finally, FIG. 12 discloses the preferred embodiment of the enteric feeding bag of the present invention, generally referenced by 210. Bag 210 differs from bags 10 and 110 in that partition 216 extends vertically upward from the bottom of the bag rather than obliquely extending upward such as partitions 16 and 116. Further, bag 210 does not employ rods 158 through partition 216 and peripheral edge flap 254 as a means of minimizing configurational distortion of feeding chamber 220. The need for of a reinforement rod 158 incorporated within partition 216 is eliminated since partition 216 is wider than both partition 16 and 116 of bags 10 and 110, respectively. By being wider, partition 216 is able to effectively dampen any configurational distortion effecting chamber 220 from fluid contained within supply chamber 218. Likewise, peripheral flap 254 is slightly wider than peripheral flap edge 154 of bag 110 further reinforcing the outer peripheral edge 256 of feeding chamber 220. Unlike flap 154, flat 254 extends further to the top of bag 210 and terminates by coinciding with a top shoulder 258 of bag 210 providing additional reinforcement for the entire length of edge 256.

Figure 12A:
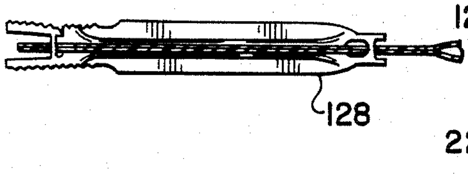
FIG. 12*a* is a horizontal section taken through line 12*a*—12*a* of FIG. 12.

Finally, FIG. 12*a* discloses a manner in which preferred clamp 128 is inserted through aperture 226 and 226' to tightly draw together the side walls of feeding chamber 220.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to a particular embodiment disclosed as the best mode contemplated for carrying out the invention, but that the invention will include all embodiments falling within the scope of the appended claims.

We claim:

1. An enteric feeding bag for fluid feeding of a patient through a feeding tube, the bag being suspendable in an operative position and having an inlet at the top and an outlet at the bottom comprising:

a supplying chamber in said bag for receiving a selected quantity of fluid, said supplying chamber being coupled to said inlet;

a feeding chamber of smaller volume than said supplying chamber, said feeding chamber being adjacent to said supplying chamber and being coupled to said outlet;

passage means between said supplying chamber and said feeding chamber placing said chambers in selected fluid communication permitting filling and refilling of said feeding chamber upon orienting said bag to a determinate position other than said operative position;

a partition between said feeding chamber and said supplying chamber, said partition having at least one discrete aperture along the length of said partition, said aperture coinciding to a selected volume of said feeding chamber; and clamping means for transversely sealing together side walls of said feeding chamber only at said aperture to define a selected volume of said feeding chamber, said clamping means forming an air impermeable seal resulting in lower air pressure within said selected volume than the ambient air pressure so that as fluid drains from said selected volume the walls of said feeding chamber defining said selected volume progressively collapse inward to trap a small residue of fluid at the bottom of said feeding.

2. The enteric feeding bag described in claim 1 wherein said partition may be provided with a plurality of discrete apertures along the length of said partition in which any one of said discrete apertures may receive said clamping means thereby providing a range of volumetric graduations to be selected from to sealably apportion said feeding chamber.

3. An enteric feeding bag for fluid feeding of a patient through a feeding tube, the bag being suspendable in an operative position and having an inlet at the top and an outlet at the bottom comprising:

a supplying chamber in said bag for receiving a selected quantity of fluid, said supplying chamber being coupled to said inlet;

a feeding chamber of smaller volume than said supplying chamber, said feeding chamber being adjacent to said supplying chamber and being coupled to said outlet;

passage means between said supplying chamber and said feeding chamber placing said chambers in selected fluid communication permitting filling and refilling of said feeding chamber upon orienting said bag to a determinate position other than said operative position;

a partition between said feeding chamber and said supplying chamber, said partition having at least one discrete aperture coinciding to any elected volume of said feeding chamber;

an appendage secured to a peripheral edge of said feeding chamber, said appendage having at least one aperture, said aperture being in horizontal alignment with said aperture on said partition; and clamping means for transversely sealing together side walls of said feeding chamber only between the aperture on said partition and the aperture on said appendage to sealably apportion said feeding chamber into a selected volume, said clamping means forming an air impermeable seal resulting in lower air pressure within said selected volume than the ambient air pressure so that as fluid evacuates said selected volume the walls of said feeding chamber defining said selected volume progressively collapse inward to trap a small residue of fluid at the bottom of said feeding chamber.

4. The enteric feeding bag described in claim 3 wherein said partition and said appendage may be provided with a plurality of discrete apertures to provide a range of volumetric graduations to be selected from to sealably apportion said feeding chamber.

5. The enteric feeding bag described in claim 4 wherein said appendage includes an elongated generally rectangular flap secured to said peripheral edge of said feeding chamber, whereby said flap mimimizes distortion of said peripheral edge when said feeding chamber contains fluid thereby maintaining a uniform peripheral configuration of said feeding chamber resulting in constant fluid dispensation from said feeding chamber.

6. The enteric feeding bag described in claim 3 wherein said clamping means is adaptable for insertion through both the aperture on said partition and through the horizontally aligned aperture on said appendage so that said clamping means cooperates with the aperture on said partition and the aperture on said appendage to stretch tranversely and drawing tautly together the side walls of the feeding chamber to sealably apportion said feeding chamber to a selected volume.

7. The enteric feeding bag described in claim 3 further including at least one semi-rigid rod incorporated into each of said partition and said appendage, said rod reinforcing and maintaining the peripheral configuration of said feeding chamber thereby assuring constant fluid dispensation from said feeding chamber.

8. The enteric feeding bag described in claim 6 wherein one of said rods are vertically and peripherally inserted into said-appendage and into said partition, the apertures on said partition and said appendage being positioned between said rods so that said clamping means abuts against said rods and cooperates with the apertures on said partition and said appendage to draw tautly together the side walls of said feeding chamber only between the apertures to sealably apportion said feeding chamber into a selected volume.

9. The enteric feeding bag described in claim 3 wherein said clamping means includes a resilient clamp, said clamp including two elongated members having flat clamping surfaces, said members being hinged together at one end and free at the other end, one member having a clasp on the free end to engage the other member thereby locking said members together and closing said clamp.

10. The enteric feeding bag described in claim 9 wherein the inner clamping surface of said other member is provided with a longitudinal ridge substantially extending the length of said other member, upon closing said clamp said ridge impresses a portion of the side wall of said feeding chamber against the inner clamping surface of said one member to impermeably seal and apportion a selected volume of said feeding chamber.

11. The enteric feeding bag described in claim 9 wherein at least said other member is outwardly and slightly arcuate between the hinged end and the free end.

12. The enteric feeding bag described in claim 9 wherein the hinged end of said resilient clamp includes an outwardly directed groove and the clasp of said clamp includes an outwardly directed groove, the groove on said clasp being adapted to fit within the aperture on said appendage and the groove on said hinged end being adapted to fit within the aperture on said partition, such that said grooves permit said clamp to stretch said appendage and said partition further apart thereby drawing tautly together the side walls of the feeding chamber to sealably apportion a selected volume of the feeding chamber.

13. The enteric feeding bag described in claim 1 or 3 wherein said partition has an upper terminus non-coinciding with the top of said bag and extending downward to coincide with the bottom of said bag.

14. The enteric feeding bag described in claim 13 wherein said partition extends obliquely downward to coincide with the bottom of said bag.

15. The enteric feeding bag described in claim 13, wherein said passage means includes a channel defined between said terminus and the top of said bag.

16. The enteric feeding bag described in claim 1, or 3 further including:

a tapered neck at the top of said bag for gripping said bag when pouring fluid through said inlet, said neck having smaller cross-sectional dimensions than said supplying chamber;

a collapsible transverse fold incorporated into said neck for developing a longitudinal throat in said supplying chamber, said fold being formed by folding over a portion of a front wall of said bag and having an opening centrally positioned to function as said inlet; and a closable inlet valve mounted onto said fold around said opening, said valve and said fold lie substantially flat and coplanar with said bag when said fold is in a non-operative position, whereby said fold may be oriented to an operative position by gripping said bag around said neck and sliding his fingers under said fold to pivot and perpendicularly dispose both said fold and valve relative to said bag while with the other hand a user pulls downward on the bottom of the bag to cause the side walls of said supplying chamber to flex symmetrically outward thereby developing said longitudinal throat.

* * * * *